(12) United States Patent
Mascarenhas

(10) Patent No.: US 7,371,813 B2
(45) Date of Patent: *May 13, 2008

(54) METHOD FOR USE OF IGF-BINDING PROTEIN FOR SELECTIVE SENSITIZATION OF TARGET CELLS IN VIVO

(75) Inventor: Desmond Mascarenhas, Los Altos Hills, CA (US)

(73) Assignee: Bioexpertise LLC, Sunnyvale, CA (US)

( * ) Notice: Subject to any disclaimer, the term of this patent is extended or adjusted under 35 U.S.C. 154(b) by 409 days.

This patent is subject to a terminal disclaimer.

(21) Appl. No.: 10/778,636

(22) Filed: Feb. 13, 2004

(65) Prior Publication Data

US 2006/0029606 A1   Feb. 9, 2006

Related U.S. Application Data

(63) Continuation of application No. 09/956,508, filed on Sep. 18, 2001.

(60) Provisional application No. 60/233,840, filed on Sep. 19, 2000.

(51) Int. Cl.
*C07K 14/71* (2006.01)
*C07K 7/08* (2006.01)
*A61K 38/10* (2006.01)
*A61K 38/17* (2006.01)

(52) U.S. Cl. .................. 530/326; 530/327; 530/303; 514/2; 514/13; 514/14

(58) Field of Classification Search ............... 530/300, 530/350, 402, 303, 326, 327; 514/2, 13, 514/14; 424/192.1
See application file for complete search history.

(56) References Cited

U.S. PATENT DOCUMENTS

| | | | |
|---|---|---|---|
| 5,187,151 A | 2/1993 | Clark et al. | |
| 5,328,891 A | 7/1994 | Baxter et al. | |
| 5,407,913 A | 4/1995 | Sommer et al. | |
| 5,527,776 A | 6/1996 | Carlino et al. | |
| 5,643,867 A | 7/1997 | Maack et al. | |
| 5,681,818 A | 10/1997 | Spencer et al. | |
| 5,723,441 A | 3/1998 | Higley et al. | |
| 5,840,673 A | 11/1998 | Buckbinder et al. | |
| 5,861,273 A | 1/1999 | Olson et al. | |
| 5,914,254 A | 6/1999 | Mascarenhas et al. | |
| 6,015,786 A | 1/2000 | Mascarenhas et al. | |
| 6,017,885 A | 1/2000 | Bagi et al. | |
| 6,025,332 A | 2/2000 | Mascarenhas | |
| 6,040,292 A | 3/2000 | Sommer | |
| 6,046,033 A * | 4/2000 | Goto et al. ................. | 435/69.4 |
| 6,368,831 B1 | 4/2002 | Maurer et al. | |
| 6,887,851 B2 * | 5/2005 | Mascarenhas ................ | 514/12 |
| 6,914,049 B2 * | 7/2005 | Mascarenhas ................ | 514/12 |

2003/0035788 A1   2/2003 Mascarenhas

FOREIGN PATENT DOCUMENTS

| | | |
|---|---|---|
| DE | 199 51 824 | 5/2001 |
| EP | 0 128 733 | 12/1984 |
| WO | WO 95/03817 | 2/1995 |
| WO | WO 95/13823 | 5/1995 |
| WO | WO 96/02565 | 2/1996 |
| WO | WO 99/63086 | 12/1999 |
| WO | WO 00/20023 | 4/2000 |
| WO | WO 00/20024 | 4/2000 |
| WO | WO 02/24216 | 3/2002 |

OTHER PUBLICATIONS

Forssmann, Accession No. AAY25506; DE19757250; published Jul. 1, 1999.*
Rosenzwig, Accession No. AAB09675; WO 2000/23469; published Apr. 17, 2000.*
Lalou, C. et al., Endocrinology, 137(8): 3206-3212, 1996.*
Sigma Catalog, Sigma Chemical Company, 1994, p. 643*
Adams, S. et al. (1995). "Pharmacokinetics and Bioavailability of rhIGF-I/IGFBP-3 in the Rat and Monkey," *Progress in Growth Factor Research* 6(2-4):347-356.
Ausubel, F. et al. (1987). *Current Protocols in Molecular Biology.* Green Publishing Associates and Wiley-Interscience, John Wiley & Sons. total pp. 6 (Table of Contents).
Baxter, R. C. et al. (Jul. 1989). "High Molecular Weight Insulin-Like Growth Factor Binding Protein Complex: Purification and Properties of The Acid-Labile Subunit From Human Serum," *The J. Biol. Chem.* 264(20):11843-11848.
Baxter, R.C. (1988). "Characterization of the Acid-Labile Subunit of the Growth Hormone—Dependent Insulin-Like Growth Factor Binding Protein Complex," *J. of Clin. Endocrinol. and Metab.* 67(2):265-272.
Baxter, R.C. et al. (Sep. 1986). "Growth Hormone-Dependent Insulin-Like Growth Factor (IGF) Binding Protein From Human Plasma Differs from Other Human IGF Binding Proteins," *Biochem. and Biophys. Res. Comm.* 139(3):1256-1261.
Blum, W.F. and Ranke, M.B. (1991). "Plasma IGFBP-3 Levels as Clinical Indicators" In *Modern Concepts of Insulin -Like Growth Factors: Plasma IGFBP-3 Levels as Clinical Indicators.* E. M. Spencer, ed., Elsevier, New York. pp. 381-393.
Buckbinder, L. et al. (1995). "Induction of the Growth Inhibitor IGF-Binding Protein 3 by P53," *Nature* 377(6550): 646-649.
Butler, A. et al. (Jul. 1998). "Stimulation of Tumor Growth by Recombinant Human Insulin-Like Growth Factor-I (IGF-I) Is Dependent on the Dose and the Level of IGF-I Receptor Expression[1]," *Cancer Res.* 58:3021-3027.
Campbell, P. G. et al. (1998). "Plasminogen Binds The Heparin-Binding Domain of Insulin-Like Growth Factor Binding Protein-3," *Am. J. Physiol.* 275(*Endocrinol. Metab. 38*):E321-E331.

(Continued)

*Primary Examiner*—Alana M. Harris
*Assistant Examiner*—Anne L. Holleran
(74) *Attorney, Agent, or Firm*—Foley & Lardner LLP

(57) ABSTRACT

New methods for the treatment of human disease are provided. IGFBP-3 is administered together with a co-administered agent to subjects having disease, thereby alleviating the symptoms of the disease, under conditions where administration of IGFBP-3 alone at the maximum practicable dose has no measurable beneficial effect on the disease condition.

2 Claims, 3 Drawing Sheets

OTHER PUBLICATIONS

Campbell, P.G. et al. (Oct. 1999). "Insulin-Like Growth Factor-Binding Protein-3 Binds Fibrinogen and Fibrin," *The J. of Biol. Chem.* 274(42)30215-30221.

Collett-Solberg, P.F. et al. (1998). "Identification of Novel High Molecular Weight Insulin-Like Growth Factor-Binding Protein-3 Association Proteins in Human Serum," *J. of Clin. Endocrinol. and Metab.* 83(8):2843-2848.

Durham, S. K.et al. (1999). "The Heparin Binding Domain of Insulin-Like Growth Factor Binding Protein (IGFBP)-3 Increases Susceptibility of IGFBP-3 to Proteolysis," *Horm. Metab. Res.* 31:216-225.

Favoni, R. E. et al. (1998). "Modulation of the Insulin-Like Growth Factor-1 System by N-(4-Hydroxyphenyl)-Retinamide in Human Breast Cancer Cell Lines," *Br. J. of Cancer* 77(12):2138-2147.

Ferry, R. J. Jr. et al. (1999). "Cellular Actions of Insulin-Like Growth Factor Binding Proteins," *Horm. Metab. Res.* 31:192-202.

Firth, S. M. et al. (Jan. 1998). "Structural Determinants of Ligand and Cell Surface binding of Insulin-Like Growth Factor-Binding Protein-3," *The J. of Biol. Chem.* 273(5):2631-2638.

Fowler, C.A. et al. (1999). "IGFBP-3 and -5 have Opposing Actions on Paclitaxel Induced Apoptosis of Human Breast Cancer Cells," *Growth Hormone and IGF Research* 9(5):368.

Fowler, C.A. et al. (2000). "Insulin-Like Growth Factor Binding Protein-3 (IGFBP-3) Potentiates Pclitaxel-Induced Apoptosis in Human Breast Cancer Cells," *Int. J. of Cancer* 88(3): 448-453.

Fowlkes, J. L. and Serra, D.M. (Jun. 1996). "Characterization of Glycosaminoglycan-Binding Domains Present in Insulin-Like Growth Factor-Binding Protein-3," *The J. of Biol. Chem*, 271(25):14676-14679.

Gill, Z.P. et al. (Oct. 1997). "Insulin-Like Growth Factor-Binding Protein (IGFBP-3) Predisposes Breast Cancer Cells To Programmed Cell Death In A Non-IGF-Dependent Manner," *The J. of Biol. Chem.* 272(41):25602-25607.

Giuliano M, et al. (Jul. 1998). "Induction of Apoptosis in Human Retinoblastoma Cells by Topoisomerase Inhibitors," *Invest. Ophthalmol. & Vis. Sci.* 39(8):1300-1311.

Jacques, G. et al. (1997). "Nuclear Localization of Insulin-Like Growth Factor Binding Protein 3 in a Lung Cancer Cell Line," *Endocrinology* 138(4):1767-1770.

Karas, M et al. (Jun. 1997). "Membrane-Associated Insulin-Like Growth Factor-Binding Protein-3 Inhibits Insulin-Like Growth Factor-I-Induced Insulin-Like Growth-Factor-I Receptor Signaling Ishikawa Endometrial Cancer Cells," *J. Biol. Chem.* 272(26):16514-16520.

Kelley, K. W. et al. (1998). "Insulin Growth Factor-I Inhibits Apoptosis in Hematopoietic Progenitor Cells: Implications in Thymic Aging[a]," *Annals New York Academy of Sciences* pp. 518-524.

Leal, S. M. et al. (Aug. 1997). "The Type V Transforming Growth Factor β Receptor is the Putatuve Insulin-Like Growth Factor-Binding 3 Receptor," *The J. of Biol. Chem.* 272(33):20572-20576.

Lee, C.Y. and Rechler, M.M. (1995). "Purified Rat Acid-Labile Subunit and Recombinant Human Insulin-Like Growth Factor (IGF)-Binding Protein-3 Can Form a 150-Kilodalton Binary Complex IN Vitro In the Absence of IGF's," *Endocrinology* 136(11):4982-4989.

Maile, L.A. et al. (1999). "The Role of Cell Surface Attachment and Proteolysis in the Insulin-Like Growth Factor (IGF)-Independent Effects of IGF-Binding Protein-3 on Apoptosis in Breast Epithelial Cells," *Endocrinology* 140(9):4040-4045.

Nickerson, T. et al. (1997). "Insulin-Like Growth Factor Binding Protein-3 Induces Apoptosis in MCF7 Breast Cancer Cells," *Biochem.and Biophys. Res. Comm.* 237(3):690-693.

Pegram, M. D. et al. (Aug. 1998). "Phase II Study of Receptor-Enhanced Chemosensitivity Using Recombinant Humanized Anti-p185[HER2/neu] Monoclonal Antibody Plus Cisplation in Patients With HER2/neu-Overexpressing Metastatic Breast Cancer Refractory to Chemotherapy Treatment," *J. of. Clin. Oncol.* 16(8):2659-2671.

Perks, C. M. et al. (1999). "Differential IGF-Independent Effects of Insulin-Like Growth Factor Binding Proteins (1-6) on Apoptosis of Breast Epithelial Cells," *J. of Cell Biochem.* 75(4):652-664.

Portera, C.A. Jr. et al. (2000). "Targeting the Insulin-LIke Growth Factor Axis in the Therapy of Colorectal Carcinoma Liver Metastasis," *Growth Hormone & IGF Research* 10(Supplement A):S47-S48.

Rajah, R.et al. (May 1997). "Insulin-Like Growth Factor (IGF)-Binding Protein-3 Induces Apoptosis and Mediates the Effects of Transforming Growth Factor-β1 on Programmed Cell Death through a p53- and IGF-Independent Mechanism," *J. of Biol. Chem.* 272(18):12181-12188.

Rajah, R. et al. (1995). "Insulin-Like Growth Factor Binding Protein (IGFBP) Proteases: Functional Regulators of Cell Growth," *Prog. in Growth Factor Res.* 6(2-4):273-284.

Rajah, R. et al. (1999). "IFGBP-3 Mediates TNF-alpha Induced Apoptosis in the Prostate Cancer Cell Line, PC-3: Role of bcl-2 Phosphorylation," *Prostate* 38(4):352-353.

Rinderknecht, E. and Humbel R.E. (Jul. 1976). "Polypeptides with Nonsuppressible Insulin-Like and Cell-Growth Promoting Activities in Human Serum: Isolation, Chemical Characterization, and some Biological Properties of Forms I and II," *Proc. Natl. Acad. Sci.* 73(7):2365-2369.

Sambrook et al. (1989). *Molecular Cloning: A Laboratory Manual*. Cold Spring Harbor Laboratory Press. 2 ed. pp. xi-xxxviii (Table of Contents).

Schedlich, L.J. et al. (Jul. 1998). "Insulin-Like Growth Factor-Binding Protein (IGFBP)-3 and IGFBP-5 Share a Common Nuclear Transport Pathway in T47D Human Breast Carcinoma Cells," *The J. of Biol. Chem.* 273(29):18347-18352.

Sommer, A et al. (1991). "Molecular Genetics and Actions of Recombinant Insulin-Like Growth Factor Binding Protein-3" *In Modern Concepts of Insulin-Like Growth Factors.* E.M. Spencer ed., Elsevier, New York pp. 715-728.

Toms, S.A. et al. (May 1998). "Antagonist Effect of Insulin-Like Growth Factor I on Protein Kinase Inhibtor-Mediated Apoptosis in Human Gliobastoma Cells in Association with bcl-2 and bcl-$X_L$," *Neurosurg.* 88:884-889.

Williams, A.C. et al. (Jan. 2000). "Increased p-53-Dependent Apoptosis by the Insulin-Like Growth Factor Binding Protein IGFBP-3 in Human Colonic Adenoma-Derived Cells[1]," *Cancer Res.* 60:22-27.

Xu, F. et al. (Feb. 1997). "Multilple Myeloma Cells are Protected Against Dexamethasone-Induced Apoptosis by Insulin-Like Growth Factors," *Br. J. of Haematol.* 97:429-440.

Yang, Y.W.H. et al. (1996). "Heparin Inhibition of Insulin-Like Growth Factor-Binding Protein-3 Binding to Human Fibroblasts and Rat Glioma Cells: Role of Heparan Sulfate Proteglycans," *Endocrinology*, 137(10):4363-4371.

Zadeh, S. and Binoux, M. (1997). "Insulin-Like Growth Factor (IGF) Binding Protein-3 Interacts with the Type 1 IGF Receptor, Reducing the Affinity of the Receptor for its Ligand: An Alternative Mechanism in the Regulation of IGF Action," *Endocrinology* 138(12):5645-5648.

Zadeh, S. and Binoux, M. (1997). "The 16-kDa Proteolytic Fragment of Insulin-Like Growth Factor (IGF) Binding Protein-3 Inhibits the Mitogenic Action of Fibroblast Growth Factor on Mouse Fibroblasts with a Targeted Disruption of the Type 1 IGF Receptor Gene," *Endocrinology* 138(7):3069-3072.

Zawada, M.W. et al. (1998). "Growth Factors Improve Immediate Survival of Embryonic Dopamine Neurons After Transplantation into Rats," *Brain Res.* 786:96-103.

\* cited by examiner

FIG. 1

FIG. 1A: IGFBP-3 SEQUENCE:
SEQ ID NO 3

GASSAGLGPVVRCEPCDARALAQCAPPPAV
CAELVREPGCGCCLTCALSEGQPCGIYTER
CGSGLRCQPSPDEARPLQALLDGRGLCVNA
SAVSRLRAYLLPAPPAPGNASESEEDRSAG
SVESPSVSSTHRVSDPKFHPLHSKIIIKK
GHAKDSQRYKVDYESQSTDTQNFSSESKRE
TEYGPCRREMEDTLNHLKFLNVLSPRGVHI
PNCDKKGFYKKKQCRPSKGRKRGFCWCVDK
YGQPLPGYTTKGKEDVHCYSMQSK

FIG. 1B: [N109D]-IGFBP-3 SEQUENCE:
SEQ ID NO 4

GASSAGLGPVVRCEPCDARALAQCAPPPAV
CAELVREPGCGCCLTCALSEGQPCGIYTER
CGSGLRCQPSPDEARPLQALLDGRGLCVNA
SAVSRLRAYLLPAPPAPGDASESEEDRSAG
SVESPSVSSTHRVSDPKFHPLHSKIIIKK
GHAKDSQRYKVDYESQSTDTQNFSSESKRE
TEYGPCRREMEDTLNHLKFLNVLSPRGVHI
PNCDKKGFYKKKQCRPSKGRKRGFCWCVDK
YGQPLPGYTTKGKEDVHCYSMQSK

Fig. 3
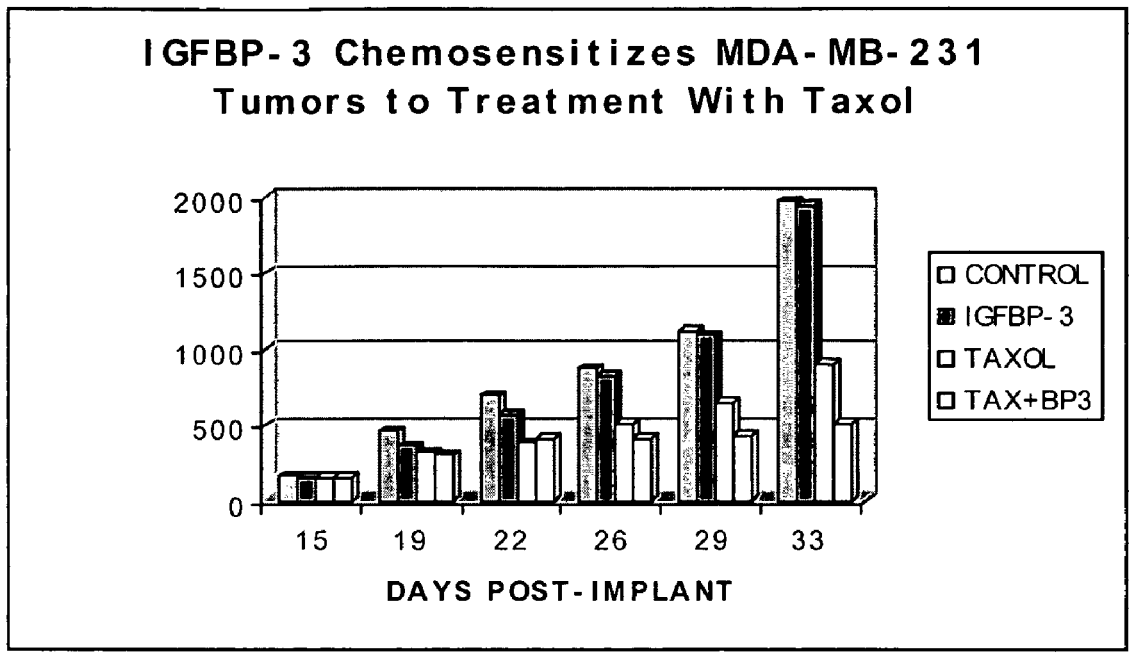
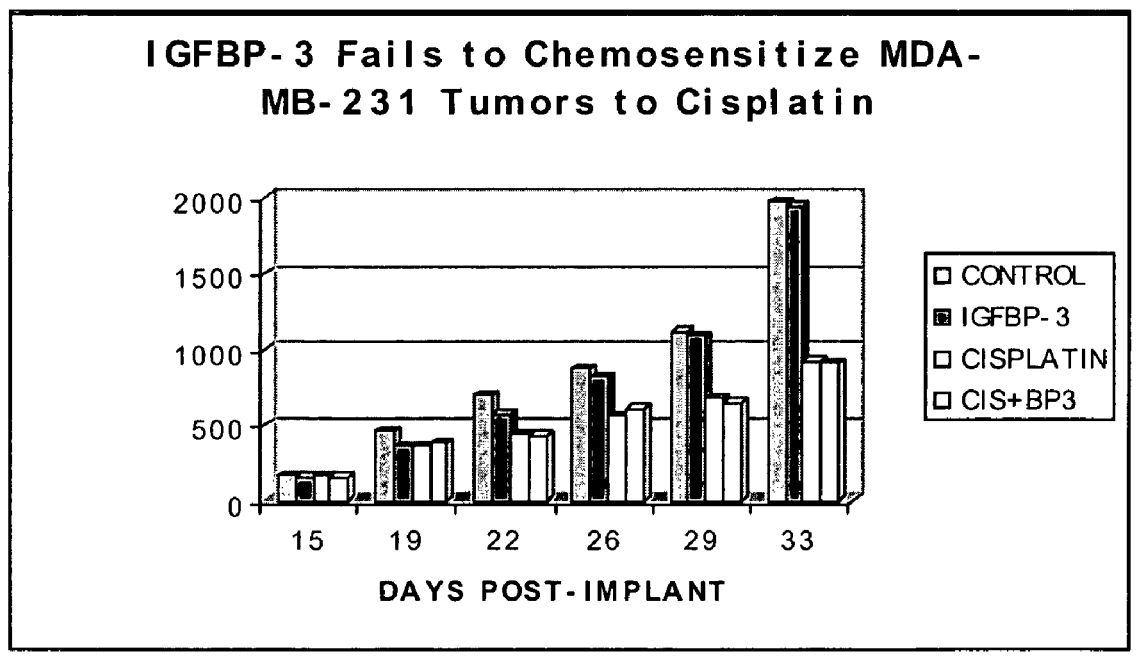

SEQUENCE LISTING

<160> NUMBER OF SEQ ID NOS: 4

<210> SEQ ID NO 1
<211> LENGTH: 23
<212> TYPE: PRT

```
<213> ORGANISM: Homo sapien

<400> SEQUENCE: 1

Asp Lys Lys Gly Phe Tyr Lys Lys Gln Cys Arg Pro Ser Lys Gly
1               5                   10                  15

Arg Lys Arg Gly Phe Cys Trp
            20

<210> SEQ ID NO 2
<211> LENGTH: 14
<212> TYPE: PRT
<213> ORGANISM: Homo sapien

<400> SEQUENCE: 2

Gln Cys Arg Pro Ser Lys Gly Arg Lys Arg Gly Phe Cys Trp
1               5                   10

<210> SEQ ID NO 3
<211> LENGTH: 264
<212> TYPE: PRT
<213> ORGANISM: Homo sapien

<400> SEQUENCE: 3

Gly Ala Ser Ser Ala Gly Leu Gly Pro Val Val Arg Cys Glu Pro Cys
1               5                   10                  15

Asp Ala Arg Ala Leu Ala Gln Cys Ala Pro Pro Pro Ala Val Cys Ala
                20                  25                  30

Glu Leu Val Arg Glu Pro Gly Cys Gly Cys Cys Leu Thr Cys Ala Leu
            35                  40                  45

Ser Glu Gly Gln Pro Cys Gly Ile Tyr Thr Glu Arg Cys Gly Ser Gly
        50                  55                  60

Leu Arg Cys Gln Pro Ser Pro Asp Glu Ala Arg Pro Leu Gln Ala Leu
65                  70                  75                  80

Leu Asp Gly Arg Gly Leu Cys Val Asn Ala Ser Ala Val Ser Arg Leu
                85                  90                  95

Arg Ala Tyr Leu Leu Pro Ala Pro Pro Ala Pro Gly Asn Ala Ser Glu
            100                 105                 110

Ser Glu Glu Asp Arg Ser Ala Gly Ser Val Glu Ser Pro Ser Val Ser
        115                 120                 125

Ser Thr His Arg Val Ser Asp Pro Lys Phe His Pro Leu His Ser Lys
130                 135                 140

Ile Ile Ile Ile Lys Lys Gly His Ala Lys Asp Ser Gln Arg Tyr Lys
145                 150                 155                 160

Val Asp Tyr Glu Ser Gln Ser Thr Asp Thr Gln Asn Phe Ser Ser Glu
                165                 170                 175

Ser Lys Arg Glu Thr Glu Tyr Gly Pro Cys Arg Arg Glu Met Glu Asp
            180                 185                 190

Thr Leu Asn His Leu Lys Phe Leu Asn Val Leu Ser Pro Arg Gly Val
        195                 200                 205

His Ile Pro Asn Cys Asp Lys Lys Gly Phe Tyr Lys Lys Lys Gln Cys
210                 215                 220

Arg Pro Ser Lys Gly Arg Lys Arg Gly Phe Cys Trp Cys Val Asp Lys
225                 230                 235                 240

Tyr Gly Gln Pro Leu Pro Gly Tyr Thr Thr Lys Gly Lys Glu Asp Val
                245                 250                 255

His Cys Tyr Ser Met Gln Ser Lys
            260
```

```
<210> SEQ ID NO 4
<211> LENGTH: 264
<212> TYPE: PRT
<213> ORGANISM: Homo sapien
<220> FEATURE:
<221> NAME/KEY: VARIANT
<222> LOCATION: (1)...(264)
<223> OTHER INFORMATION: [N109D]-hIGFBP-3 derivative.  A non-naturally
      occurring derivative.

<400> SEQUENCE: 4

Gly Ala Ser Ser Ala Gly Leu Gly Pro Val Val Arg Cys Glu Pro Cys
 1               5                  10                  15

Asp Ala Arg Ala Leu Ala Gln Cys Ala Pro Pro Ala Val Cys Ala
             20                  25                  30

Glu Leu Val Arg Glu Pro Gly Cys Gly Cys Cys Leu Thr Cys Ala Leu
             35                  40                  45

Ser Glu Gly Gln Pro Cys Gly Ile Tyr Thr Glu Arg Cys Gly Ser Gly
         50                  55                  60

Leu Arg Cys Gln Pro Ser Pro Asp Glu Ala Arg Pro Leu Gln Ala Leu
65                  70                  75                  80

Leu Asp Gly Arg Gly Leu Cys Val Asn Ala Ser Ala Val Ser Arg Leu
                 85                  90                  95

Arg Ala Tyr Leu Leu Pro Ala Pro Pro Ala Pro Gly Asp Ala Ser Glu
                100                 105                 110

Ser Glu Glu Asp Arg Ser Ala Gly Ser Val Glu Ser Pro Ser Val Ser
                115                 120                 125

Ser Thr His Arg Val Ser Asp Pro Lys Phe His Pro Leu His Ser Lys
        130                 135                 140

Ile Ile Ile Ile Lys Lys Gly His Ala Lys Asp Ser Gln Arg Tyr Lys
145                 150                 155                 160

Val Asp Tyr Glu Ser Gln Ser Thr Asp Thr Gln Asn Phe Ser Ser Glu
                165                 170                 175

Ser Lys Arg Glu Thr Glu Tyr Gly Pro Cys Arg Arg Glu Met Glu Asp
                180                 185                 190

Thr Leu Asn His Leu Lys Phe Leu Asn Val Leu Ser Pro Arg Gly Val
                195                 200                 205

His Ile Pro Asn Cys Asp Lys Lys Gly Phe Tyr Lys Lys Lys Gln Cys
        210                 215                 220

Arg Pro Ser Lys Gly Arg Lys Arg Gly Phe Cys Trp Cys Val Asp Lys
225                 230                 235                 240

Tyr Gly Gln Pro Leu Pro Gly Tyr Thr Thr Lys Gly Lys Glu Asp Val
                245                 250                 255

His Cys Tyr Ser Met Gln Ser Lys
                260
```

METHOD FOR USE OF IGF-BINDING PROTEIN FOR SELECTIVE SENSITIZATION OF TARGET CELLS IN VIVO

CROSS REFERENCE TO RELATED APPLICATIONS

This application is a continuation of U.S. application Ser. No. 09/956,508, filed on Sep. 18, 2001 which claims priority under 35 USC § 119(e) to U.S. Provisional Application Ser. No. 60/233,840, filed Sep. 19, 2000, which is incorporated by reference herein.

TECHNICAL FIELD

The invention relates to the field of treatment of disease, and particularly to the use of insulin-like growth factor binding protein for selective sensitization of target cells in vivo.

BACKGROUND ART

Growth factors are polypeptides which stimulate a wide variety of biological responses (e.g. DNA synthesis, cell division, expression of specific genes, etc.) in a defined population of target cells. A variety of growth factors have been identified, including the transforming growth factor beta family (TGF-βs), epidermal growth factor and transforming growth factor alpha (the TGF-αs), the platelet-derived growth factors (PDGFs), the fibroblast growth factor family (FGFs) and the insulin-like growth factor family (IGFs), which includes IGF-I and IGF-II. Many growth factors have been implicated in the pathogenesis of cancer.

IGF-I and IGF-II (the "IGFs") are related in amino acid sequence and structure, with each polypeptide having a molecular weight of approximately 7.5 kilodaltons (kDa). IGF-I mediates the major effects of growth hormone, and is thus the primary mediator of growth after birth. IGF-I has also been implicated in the actions of various other growth factors, since the treatment of cells with such growth factors leads to increased production of IGF-I. In contrast, IGF-II is believed to have a major role in fetal growth. Both IGF-I and IGF-II have insulin-like activities (hence their names), and are mitogenic (stimulate cell division).

IGF-I has been found to stimulate the growth of cells from a number of different types of cancer (Butler et al., 1998 Cancer Res. 58(14):3021-3027; Favoni R E, et al., 1998, Br. J. Cancer 77(12): 2138-2147). Additionally, IGF-I has additionally been found to exert anti-apoptotic effects on a number of different cell types, including tumor cells (Giuliano M, et al., 1998 Invest Ophthalmol. Vis. Sci. 39(8): 1300-1311; Zawada W M, et al., 1998, Brain Res. 786(1-2): 96-103; Kelley K W, et al., 1998, Ann. N. Y. Acad. Sci. 840: 518-524; Toms S A, et al., 1998, J. Neurosurg. 88(5): 884-889; Xu F, et al., 1997, Br. J. Haematol. 97(2): 429-440). Prospective studies have implicated IGF-I as a risk factor for cancers of the prostate, breast, and colon, while IGFBP-3, the major circulatory binding protein for IGFs, appears to have a protective effect. A variety of other observations further support the idea that the relative balance of IGFBP-3 to other IGF-binding proteins (notably IGFBP-2) is somehow instrumental in the control of tumor cell growth, both in vitro and in vivo. Recent evidence also suggests that IGFBP-3 may play a central role in the growth and apoptosis of tumor cells in an IGF-independent manner.

Approximately half of the 1.3 million patients diagnosed with cancer each year in the U.S. have (or will be at risk for) systemic disease. Chemotherapy is the most common therapeutic approach for these patients. Most chemotherapeutic agents are effective primarily against dividing cells, and myelosuppression is often the dose-limiting toxicity. Chemical agents fall into several categories and have different mechanisms of action but, at effective doses, most have side-effects which seriously impact the patient's quality of life. doxorubicin (ADRIAMYCIN®), irinotecan (CPT-11), paclitaxel (TAXOL®), cisplatin, tamoxifen, methotrexate and 5-fluorouracil are popular agents used to treat a variety of cancers, sometimes in combination. In addition to myelosuppression, gastrointestinal effects, mucositis, alopecia, and (in the case of doxorubicin) cardiac toxicities are also observed with these agents.

Clearly, it would be of interest to find ways to make tumor cells selectively sensitive to these chemical agents. One approach might be to target the very properties that make cancer cells unique. Cancer cells generally evolve strategies for circumventing the normal cell cycle checkpoint controls that target cells for self-destruction after sustaining the kind of DNA damage typically inflicted by chemotherapeutic agents. If such functions could be even partially restored in tumor cells by pretreatment with a "sensitizing" agent, one would predict that such treatment would exert a selective effect on such cells.

Almost all IGF circulates in a non-covalently associated complex of IGF-I, insulin-like growth factor binding protein 3 (IGFBP-3) and a larger protein subunit termed the acid labile subunit (ALS), such that very little free IGF-I is detectable. The ternary complex is composed of equimolar amounts of each of the three components. ALS has no direct IGF-binding activity and appears to bind only to the IGF/IGFBP-3 complex (Baxter et al., J. Biol. Chem. 264(20): 11843-11848, 1989), although some reports suggest that IGFBP-3 can bind to rat ALS in the absence of IGF (Lee et al., Endocrinology 136:4982-4989, 1995). The ternary complex of IGF/IGFBP-3/ALS has a molecular weight of approximately 150 kDa and has a substantially increased half-life in circulation when compared to binary IGF/IGFBP-3 complex or IGF alone (Adams et al., Prog. Growth Factor Res. 6(2-4):347-356; presented October 1995, published 1996). This ternary complex is thought to act "as a reservoir and a buffer for IGF-I and IGF-II preventing rapid changes in the concentration of free IGF" (Blum et al. (1991), "Plasma IGFBP-3 Levels as Clinical Indicators" in MODERN CONCEPTS OF INSULIN-LIKE GROWTH FACTORS, pp. 381-393, E. M. Spencer, ed., Elsevier , New York). While there is essentially no excess (unbound) IGFBP-3 in circulation, a substantial excess of free ALS does exist (Baxter, J. Clin. Endocrinol. Metab. 67:265-272, 1988).

How IGFBP-3 mediates its cellular effects is not well understood, although there is indirect evidence to suggest that it mediates some of the effects of p53, a well-characterized tumor suppressor (Ferry et al., (1999) Horm Metab Res 31(2-3):192-202). IGFBP-3 is mobilized to the nucleus of rapidly growing cells (Schedlich, et al., (1998) J. Biol. Chem. 273(29):18347-52; Jaques, et al., (1997) Endocrinology 138(4):1767-70). A useful step toward defining the functional interactions of IGFBP-3 would be to identify protein domains involved in the ability of IGFBP-3 to specifically bind a surprisingly large array of intracellular and extracellular targets. Known targets include: IGF-I, IGF-II, insulin (under some conditions), acid-labile subunit (ALS), plasminogen, fibrinogen, transferrin, lactoferrin, collagen Type Ia, prekallikrein, RXR-alpha, viral oncoproteins, heparin, specific proteases, cellular receptors, a number of intracellular targets identified in two-hybrid screens, and components of the nuclear localization transport machinery (Mohseni-Zadeh and Binoux (1997) *Endocrinology* 138 (12):5645-8; Collett-Solberg, et al. (1998) *J. Clin. Endocrinol Metab.* 83(8):2843-8; Rajah, et al. (1995) *Prog. Growth Factor Res.* 6(2-4):273-84; Fowlkes and Serra (1996) *J. Biol. Chem.* 271:14676-14679; Campbell, et al. (1999) *J. Biol Chem.* 274(42):30215-21; Durham, et al. (1999) *Horm Metab Res* 31(2-3):216-25; Campbell, et al. (1998) *Am J Physiol.* 275(2Pt 1):E321-31). A better understanding of these binding interactions might allow the generation of IGFBP-3 variants lacking one or more of these functions. The activity of these and other variants in in vivo models may suggest novel therapeutic strategies based either on the variant proteins themselves, mimetics, or small organic molecules selected from combinatorial chemistry libraries created with the information gained from a study of these variants.

A recently described mutant in which residues 228-232 of IGFBP-3 have been substituted with the corresponding residues from IGFBP-1 (a closely related protein) shows impaired binding to ALS, RXR-alpha, and plasminogen (Campbell, et al. (1998) *Am. J. Physiol.* 275(2 Pt 1):E321-31; Firth, et al. (1998) *J. Biol. Chem.* 273:2631-2638). Specific proteolysis of IGFBP-3 under certain physiological conditions such as pregnancy and critical illness can lead to altered binding and release of its IGF ligand. The binary complex of IGFBP-3 with IGF-I or IGF-II (both growth factors bind IGFBP-3, with similar affinities) can extravasate across endothelial junctions to the intercellular milieu where IGFBP-3 can interact specifically with glycosaminoglycans, specific proteases, and cell-surface proteins.

It should be noted that, while IGFBP-3 is the most abundant of the IGF binding proteins ("IGFBPs"), at least five other distinct IGFBPs have been identified in various tissues and body fluids. Although these proteins bind IGFs, they originate from separate genes and have distinct amino acid sequences. Unlike IGFBP-3, other circulating IGFBPs are not saturated with IGFs. IGFBP-3 and IGFBP-5 are the only known IGFBPs which can form the 150 kDa ternary complex with IGF and ALS. The IGF and ALS binding domains of IGFBP-3 are thought to be in the N-terminal portion of the protein, as N-terminal fragments of the protein isolated from serum retain these binding activities. However, some of the other IGFBPs have also been suggested for use in combination with IGF-I as therapeutics.

In addition to its role as the major carrier protein for IGF in serum, IGFBP-3 has been recently shown to have a number of different activities. IGFBP-3 can bind to an as-yet unidentified molecule on the cell surface, where it can inhibit the activity of exogenously-added IGF-I (Karas et al., 1997, *J. Biol. Chem.* 272(26):16514-16520). Although the binding of IGFBP-3 to cell surfaces can be inhibited by heparin, the unidentified cell surface binding molecule is unlikely to be a heparin-like cell surface glycosaminoglycan, because enzymatic removal of heparin glycosaminoglycans has no effect on IGFBP-3 cell surface binding (Yang et al., 1996, *Endocrinology* 137(10):4363-4371). It is not clear if the cell surface binding molecule is the same or different than the IGFBP-3 receptor that was identified by Leal et al. (1997, *J. Biol. Chem.* 272(33):20572-20576), which is identical to the type V transforming growth factor-beta (TGF-β) receptor.

IGFBP-3, when used alone in in vitro assays, has also been reported to promote apoptosis. Interestingly, IGFBP-3 has been shown to promote apoptosis in cells with and without functional type 1 IGF receptors (Nickerson et al., 1997, *Biochem. Biophys. Res. Comm.* 237(3):690-693; Rajah et al., 1997, *J. Biol. Chem.* 272(18):12181-12188). However, there are conflicting reports as to whether apoptosis is induced by full length IGFBP-3 or a proteolytic fragment of IGFBP-3 (Rajah et al., *ibid*; Zadeh et al., 1997, *Endocrinology* 138(7):3069-3072). More recently, a wealth of unpublished data gathered in a number of laboratories fails to support some of the claims made in the above publications. In in vivo models tested to date, infused IGFBP-3 protein alone has showed mixed results in limiting tumor growth.

U.S. Pat. No. 5,681,818 claims the administration of IGFBP-3 for controlling the growth of somatomedin dependent tumors in the treatment of cancer. U.S. Pat. No. 5,840,673 also describes the indirect intracellular modulation of IGFBP-3 levels as a method for controlling tumor growth. U.S. Pat. No. 6,015,786 discloses the use of IGFBP-3 complexed with mutant IGF for the treatment of IGF-dependent tumors. However, each of these patents discloses a direct in vivo effect of administered IGFBP-3 protein on tumor growth. None of these patents envisages a situation where IGFBP-3 has no effect on tumors on its own, yet sensitizes tumors to the action of other agents. Numerous publications (Williams, et al., *Cancer Res* 60(1):22-7, 2000; Perks, et al., *J Cell Biochem* 75(4):652-64, 1999; Maile et al., *Endocrinology* 140(9):4040-5, 1999; Gill, et al., *J Biol Chem* 272(41):25602-7, 1997) further demonstrate combined effects of IGF binding proteins, radiation and ceramide on cultured cells. However, it is difficult or impossible to extrapolate from tissue culture results to effectiveness in vivo. In one report (Portera et al, *Growth Hormone & IGF Research* 2000, Supplement A, S49-S50, 2000) IGFBP-3 combined with CPT-11 showed additive effects in a colon cancer model both in vivo and in vitro, but IGFBP-3 alone also showed effects on tumor growth in this model. At the present time, a widely held belief among skilled practitioners in the field is that IGFBP-3 alone may sometimes control tumor growth directly. No one has shown that systemically administered IGFBP-3 can sensitize tumor cells in animals to the action of co-administered agents, without inhibiting tumor growth when used on its own at similar doses.

Such a distinction is of considerable practical importance. Among other things, it means that many types of tumors that may appear to be recalcitrant to IGFBP-3 treatment when used singly, or to some other agent used on its own, may in fact be quite susceptible to the combination. Unless this fact is appreciated, even the testing of certain combinations of substances which, on their own, are known to have no effects on tumor growth, may never be undertaken.

IGF-I and IGFBP-3 may be purified from natural sources or produced by recombinant means. For instance, purification of IGF-I from human serum is well known in the art (Rinderknecht et al. (1976) *Proc. Natl. Acad. Sci. USA* 73:2365-2369). Production of IGF-I by recombinant processes is shown in EP 0 128 733, published in December of 1984. IGFBP-3 may be purified from natural sources using a process such as that shown in Baxter et al. (1986, *Biochem. Biophys. Res. Comm.* 139:1256-1261). Alternatively, IGFBP-3 may be synthesized by recombinantly as discussed in Sommer et al., pp. 715-728, MODERN CONCEPTS OF INSULIN-LIKE GROWTH FACTORS (E. M. Spencer, ed., Elsevier, New York, 1991). Recombinant IGFBP-3 binds IGF-I in a 1:1 molar ratio.

Topical administration of IGF-I/IGFBP-3 complex to rat and pig wounds is significantly more effective than administration of IGF-I alone (Id.). Subcutaneous administration of IGF-I/IGFBP-3 complex to hypophysectomized, ovariectomized, and normal rats, as well as intravenous administration to cynomolgus monkeys, "substantially prevents the hypoglycemic effects" of IGF-I administered alone (Id.).

The use of IGF/IGFBP-3 complex has been suggested for the treatment of a wide variety of disorders (see, for example, U.S. Pat. Nos. 5,187,151, 5,527,776, 5,407,913, 5,643,867, 5,681,818 and 5,723,441, as well as International Patent Applications Nos. WO 95/03817, WO 95/13823, and WO 96/02565. IGF-I/IGFBP-3 complex is also under development by Insmed Pharmaceuticals, Inc., as a treatment for several indications, including diabetes and recovery from hip fracture surgery.

For practitioners skilled in the art, the complex of IGF-I and IGFBP-3 is generally considered to be a different compound, and to have different biological effects, than IGFBP-3 alone.

While there are a large number of cytotoxic drugs available for the treatment of cancer, these drugs are generally associated with a variety of serious side effects, including alopecia, leukopenia, mucositis. Accordingly, there is a need in the art for cancer therapies that do not induce the serious side effects associated with conventional cytotoxic chemotherapy. One method for achieving this goal is to make target cells (such as tumor cells) selectively sensitive to cytotoxic drugs, thereby permitting the effective use of such drugs at lower doses not associated with serious side effects.

A number of reports claim IGFBP-3 alone can cause apoptosis in tumor cells in culture, and others have described additive effects of combining IGFBP-3 treatment with various chemical agents in tissue culture (cited above). However, it is unclear how these effects relate, if at all, to in vivo models.

The key assumption in all of the above examples is that the efficacy of combination treatments involving administration of IGFBP-3 and other agents is investigated only after IGFBP-3 has shown efficacy on its own. Given this state of thinking, which is established in the field at this time, it is therefore unlikely that effective combination regimens will be identified unless IGFBP-3 alone is shown to have efficacy in the first place. Synergistic effects with co-administered agents showing marginal efficacy themselves would be even harder to identify.

Herceptin, a humanized antibody used in the treatment of breast cancer, has exemplified the use of large proteinaceous molecules to extend the therapeutic efficacy of chemical agents (Pegram, et al. (1998) *J. Clin. Oncol.* 16(8):2659-71). However, this molecule was approved for clinical use based on its own efficacy on tumors and survival, when used alone. Additive effects have been observed when this molecule is administered in combination with chemical agents.

DISCLOSURE OF THE INVENTION

The inventor has surprisingly found that IGFBP-3 may not be generally effective in controlling tumor growth when used alone, as was previously postulated by several investigators. Nevertheless, the inventor has found that IGFBP-3 is effective in synergistically sensitizing tumor cells to the stressful effects of co-administered agents such as adriamycin and taxol, when administered systemically to animals in doses at which IGFBP-3 itself is ineffective in controlling tumor growth when administered alone. This was true even when the dose of IGFBP-3 used in the experiment approximated the maximum practical dose of IGFBP-3 usable in a clinical scenario for economic, technical, or other reasons.

This finding was unexpected because IGFBP-3 had previously been thought to control tumor cell growth on its own (Sommer et al., supra), based on the in vitro data. The synergistic sensitization phenomenon disclosed herein may also explain why IGFBP-3 has been sporadically associated with negative effects on cell survival. The combination of stress or damage (whether chemically induced, biologically induced, physically induced, or otherwise effected by cell culture conditions) and IGFBP-3 administration may be the true cause of apoptosis in such cases. One way to show this directly is to place cultured tumor cells under nutritional stress by growing them at sub-optimal nutrient concentrations. By the line of thinking posited above, the subsequent addition of IGFBP-3 should have a dramatically greater effect on cell death (apoptosis), than the same dose of IGFBP-3 added to the same cell line growing under normal nutrient concentrations.

Disclosed herein are methods for alleviating the symptoms of disease. In one embodiment, an effective amount of IGF-binding protein or derivative thereof is systemically co-administered with a chemotherapeutic agent to a subject having cancer, thereby alleviating the symptoms of the cancer.

In another embodiment, IGF-binding protein or a derivative thereof is systemically co-administered with other biological modifiers such as ligands of retinoid or thyroid receptors, or antibodies capable of binding target cell molecules, to the subject with disease.

In yet another embodiment, IGF-binding protein or derivative thereof is administered as described in the other embodiments, but the administration occurs indirectly, using a gene sequence delivered by a viral vector or other vehicle, or using an inducer or antagonist.

In certain aspects, the invention provides methods for alleviating the symptoms of cancer, by administering a co-administered agent together with an effective amount of insulin-like growth factor binding protein-3 (IGFBP-3) or derivative thereof to a subject having cancer under conditions wherein the administration of IGFBP-3 or derivative alone does not alleviate said symptoms of cancer.

In some embodiments, the co-administered agent is a chemical agent selected from the group consisting of alkylating agents, antimetabolites, Vinca alkaloids, podophyllotoxins, antitumor antibiotics, nitrosoureas, metallic DNA modifying compounds and microtubule stabilizers, a biological agent selected from the group consisting of nutrient limitation, antibodies, vaccines, peptides, cytokines, receptor ligands and nucleic acids, or a a physical agent selected from the group consisting of heat, pressure, osmolarity, acidity and radiation. Preferred co-administered agents include chemical agents selected from the group consisting of doxorubicin, paclitaxel, methotrexate, tamoxifen, cyclophosphamide, vincristine, etoposide, streptozotocin and 5-fluorouracil.

In certain embodiments, the cancer treated is breast, prostate, colon, ovarian, pancreatic, gastric or lung cancer.

In some embodiments, the IGFBP-3 is administered at about 0.01 to about 50 milligrams per kilogram total body weight per day (mg/kg/day).

BRIEF DESCRIPTION OF THE DRAWINGS

FIG. 1 shows sequences IGFBP-3 in single letter amino acid code. FIG. 1A shows the amino acid sequences of native human IGFBP-3 (Ala$_5$ allelic variant). FIG. 1B shows [N109D]-hIGFBP-3 derivative (Ala$_5$ allelic variant).

FIG. 3 depicts the results of the experiment described in Example 2. The upper panel shows the effects of IGFBP-3 and paclitaxel (TAXOL®) on MDA-MB-231 cells implanted in mice. At each time point, the columns show, left to right, control, IGFBP-3 alone, paclitaxel alone, and IGFBP-3 plus paclitaxel. The lower panel shows the effects of IGFBP-3 and cisplatin on MDA-MB-231 tumors implanted in mice. At each time point, the columns show, left to right, control, IGFBP-3 alone, cisplatin alone, and IGFBP-3 plus cisplatin.

BEST MODE FOR CARRYING OUT THE INVENTION

Figure 2:
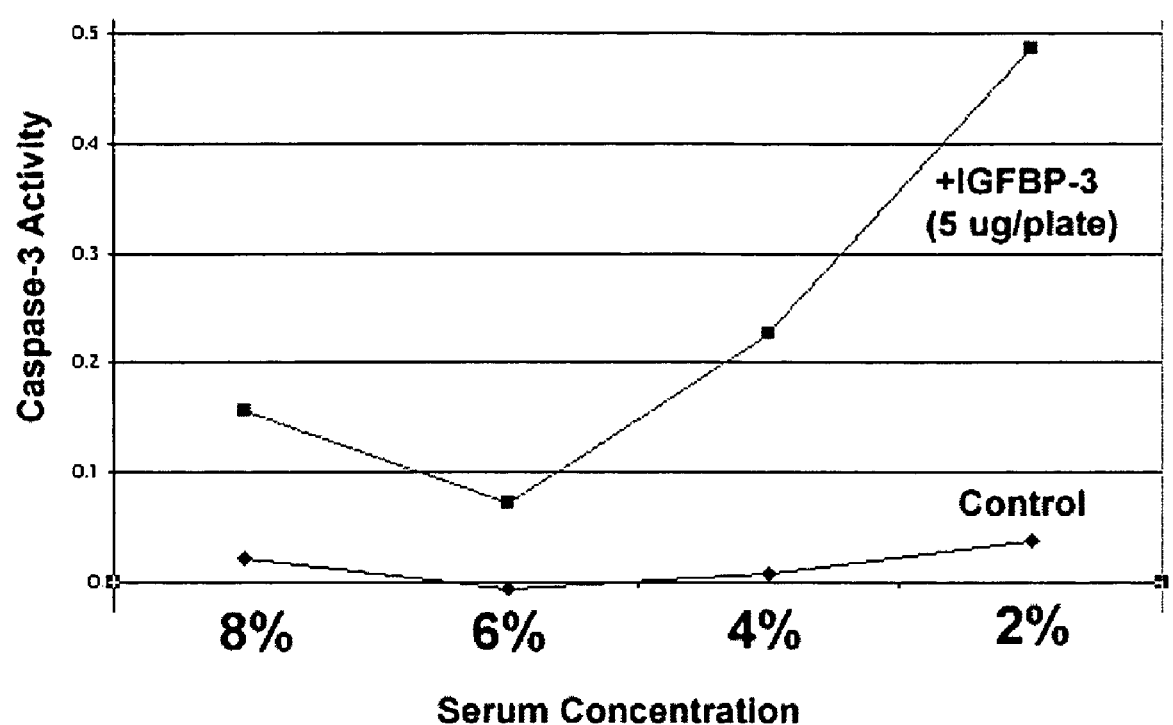
FIG. 2 depicts the results of the experiment described in Example 1. The upper panel shows the effects of IGFBP-3 and 5-fluoruracil (5-FU) on 16C mammary adenocarcinoma cells implanted in mice. At each time point the columns show, left to right, control, IGFBP-3 alone, 5-FU alone, and IGFBP-3 plus 5-FU. The lower panel shows the effects of IGFBP-3 and doxorubicin (ADRIAMYCIN®) on 16C mammary adrenocarcinoma cells implanted in mice. At each time point the columns show, left to right, control, IGFBP-3 alone, doxorubicin alone, and IGFBP-3 plus doxorubicin.

Disclosed herein are new methods for the treatment of cancer. An effective amount of IGFBP-3 and a co-administered agent are systemically administered to a subject suffering from cancer, thereby alleviating the symptoms of the cancer. The combined effects of the IGFBP-3 and the chemical insult synergistically slow the growth rate of cancer, thereby alleviating the symptoms of, or slowing the progression of the cancer. While not wishing to be bound by any particular theory, the inventor believes that the administration of IGFBP-3 restores a more "normal" response within tumor cells to cell cycle checkpoints. When simultaneously stressed by chemical or radiation damage, the tumor cells become more responsive to apoptotic signals in the presence of IGFBP-3.

The inventor has surprisingly found that systemic administration of IGFBP-3 alone at the substantial dose of 4 mg/kg for 21 days was completely ineffective at slowing tumor growth in more than one animal model of cancer. This was surprising because it was believed that IGFBP-3 alone could cause the death of some tumor cells. The dose chosen is likely to be close to the maximum practicable dose that would be systemically delivered in a human clinical setting. The maximum practicable dose is determined by the cost, pharmacokinetics, toxicology, solubility of the formulation, route of administration, and other practical considerations.

Definitions

As used herein, the terms "IGF-binding protein" and "IGFBP" refer to natural and derivative molecules based on any of the six human insulin-like growth factor binding proteins 1 through 6. "Derivatives" refers to point mutants, deletion mutants, peptides, peptidomimetics, small organic molecules, nucleic acids (such as RNAs), or any other molecules which retain, modify or mimic those structural properties of IGFBPs that are relevant to their ability to sensitize target cells. Derivatives also include nucleic acid molecules encoding IGF-binding proteins, such as DNA gene sequences.

The term "co-administered agent", as used herein, refers to a chemical agent; a biological agent such as an antibody, vaccine, nutrient, cytokine, nucleic acid or receptor ligand such as growth factor, retinoid or thyroid receptor ligand; and a physical agent, such as radiation, acidity and heat. Co-administered agents preferably have an anti-tumor activity when administered in the absence of IGFBP.

"Chemical agents" include all common chemotherapeutic agents such as alkylating agents (e.g. busulfan, cyclophosphamide, ifosfamide), antimetabolites (e.g. Ara-C, 5-fluorouracil, methotrexate), Vinca alkaloids (e.g. vinblastine, vincristine), podophyllotoxins (e.g. VM-26, etoposide), antibiotics (e.g. bleomycin, doxorubicin/ADRIAMYCIN®), nitrosoureas (e.g. BCNU, streptozotocin), and metallic DNA modifying compounds (e.g. carboplatin, cisplatin), and microtubule stabilizers (e.g., paclitaxel/TAXOL®). Chemical agents also include chemical compounds that directly affect a targeted receptor by reducing levels of the cognate ligand, by acting on the targeted receptor or acting on the signalling pathway of the targeted receptor. For example, the thyroid axis may be indirectly manipulated via antagonists such as thyroid axis antagonists. As an example, the term "thyroid axis antagonist" refers to a compound which acts to decrease thyroid hormone activity in a subject. Thyroid axis antagonists include 6-n-propyl-2-thiouracil (propylthiouracil or PTU), methimazole, carbimazole, and other compounds known to the art to reduce thyrotropic hormones, thyroid hormones, or thyroid receptor signaling.

The term "treatment regimen" refers to a course of therapy. Treatment regimens may utilize a single agent such as a single chemical agent, but more typically involve two or more different agents (e.g., combination therapy with multiple different cytotoxic chemotherapry agents), and may involve two or more different types of agents (e.g., administration of a chemical agent such as paclitaxel in combination with a physical agent such as ionizing radiation).

The term "alleviating", as used herein, refers to an improvement, lessening, or diminution of a symptom of cancer. "Alleviating" also includes slowing or halting progression of a symptom.

The term "subject", as used herein, refers to a vertebrate individual, including avian and mammalian individuals, and more particularly to sport animals (e.g., dogs, cats, and the like), agricultural animals (e.g., cows, horses, sheep, and the like), and primates (e.g., humans).

As used herein, the term "comprising" and its cognates are used in their inclusive sense; that is, equivalent to the term "including" and its corresponding cognates.

As used herein, the singular form "a", "an", and "the" includes plural references unless indicated otherwise.

IGF-binding protein, in combination with agents causing cellular damage or stress, may be used to treat any cancer, preferably carcinomas such as breast, prostate, colon and lung cancers. Treatment with IGF-binding protein in combination with an agetn which causes cellular damage or stress alleviates at least one symptom of the cancer being treated. The particular symptom alleviated will, as will be understood by one of skill in the art, vary depending on the type of cancer, location of the primary tumor and any local, regional, or distant spread, and the natural history of the particular cancer. Alleviation of symptoms by administration of an IGF-binding protein in combination with an agent may include, but are not limited to, reduction in or elimination of tumor size, reduction in or elimination of tumor-related pain, prevention of or an increased time to disease progression, elimination or reduction of symptoms secondary to the cancer (e.g., reduction or elimination of a bowel obstruction due to a colon tumor), increased disease free interval, and increased overall survival time.

IGF-binding protein for use in accordance with the instant inventive methods may be derived from any species, although species-matched IGF-binding protein (i.e., IGF-binding protein or derivative based on the native sequence from the same species as the subject to which the IGF-binding protein is to be administered) is preferred. IGF-binding protein for use in the instant invention is uncomplexed IGF-binding protein, that is, administered in the absence of IGF (e.g., not administered as IGF-I/IGFBP-3 complex), and is preferably administered without any IGF protein.

One of the naturally occurring protein sequences for IGFBP-3 is shown in FIG. 1. Human IGFBP-3 is found in two naturally occuring allelic variants; alanine may be found at position 5 of the mature protein (shown in FIG. 1a), or alternately glycine may be found in this position. Additionally, other variants of IGFBP-3 may be created. For example, [N109D]-IGFBP-3 is a derivative of IGFBP-3 that has an amino acid sequence alteration at position 109 of the mature sequence but behaves very similarly to wild type IGFBP-3 in most assays tested to date. Point mutant derivatives also include mutants selectively debilitated in their ability to bind IGF-I, IGF-II, or any other known ligands of IGFBPs. For example, it has been shown that point mutations at positions corresponding to one or more of the conserved or semi-conserved residues $Val_{49}$, $Tyr_{50}$, $Pro_{62}$, $Lys_{68}$, $Pro_{69}$, $Leu_{70}$, $Ala_{72}$, $Leu_{73}$, and $Leu_{74}$ of IGFBP-5 may be debilitated in IGF-I binding. Many of these residues are well-conserved in the other IGF-binding proteins as well. Mutations at positions 228 and 230 of the mature sequence of IGFBP-3 are believed to affect nuclear translocation and binding to extracellular matrix proteins such as collagen.

Deletion mutants of IGFBP-3 or peptide derivatives based on parts of the IGFBP-3 sequence, may also be used. The IGFBP-3 molecule consists of 264 amino acids and has three major structural domains. The cysteine-rich amino terminal domain (roughly the first 100 amino acids of the mature sequence) is known to be essential for high-affinity binding of IGFs. The middle domain (about 80 amino acids) has no cysteine residues, and is very susceptible to proteases. It may also play a role in binding specific cellular receptors. The carboxy-terminal domain (about 80 amino acids) is also cysteine-rich and contains sequences essential for binding extracellular matrix molecules such as heparin and collagen, serum molecules such as ALS, plasminogen, and fibrinogen, nuclear receptors such as RXR, and importin. Methods for nucleic acid manipulation, protein expression and protein purification for obtaining deletion or point mutants are known in the art.

Once a domain of IGFBP-3 has been defined by point mutation or deletion analysis as necessary and sufficient for a particular biological activity, such as the sensitization of target cells, it is possible to design smaller molecules, such as peptides, consisting of part of the IGFBP sequence. For example, one or both of the sequences:

```
(H2N) . . . DKKGFYKKKQCRPSKGRKRGFCW . . . (COOH);
(SEQ ID NO: 1);
and (H2N) . . . QCRPSKGRKRGFCW . . . (COOH)
(SEQ ID NO: 2)
``` may be sufficient to mimic some of the biological effects of IGFBP-3.

Also disclosed herein is a methodology for creating and recovering such derivative molecules. As disclosed in Example 5, the inventor has discovered the presence of a metal-binding motif in the IGFBP-3 molecule, allowing practical recovery of domains containing this motif. Also disclosed are methods for generating properly folded sub-domains of IGFBP-3, by engineering target sites for a specific protease at strategic locations in the IGFBP-3 sequence, expressing the construct, and cleaving the expressed protein with the cognate protease. The significance of this approach in the case of IGFBP-3 is that numerous unsuccessful attempts have already been made, in a number of laboratories, to express truncated segments of IGFBP-3 in properly folded form. To date, these have proved relatively unsuccessful in generating such properly folded molecules as a major percentage of the total expressed product. By generating the intact molecule and cleaving it post facto, it is possible to generate folded domains with substantially higher efficiencies.

Small organic molecules designed or selected based on the IGFBP-3 sequence may also be created by computational and other methods. Any of these derivative molecules may be assayed for the desired biological activities, including the ability to sensitize target cells to chemical treatments. Based on the results of these assays, a small number of IGFBP-3 mutants or derivatives with altered characteristics may be selected for clinical testing in the context of human disease.

The IGF-binding protein or derivative is normally produced by recombinant methods, which allow the production of all possible variants in IGFBP sequence. Techniques for the manipulation of recombinant DNA are well known in the art, as are techniques for recombinant production of proteins (see, for example, in Sambrook et al., MOLECULAR CLONING: A LABORATORY MANUAL, Vols. 1-3 (Cold Spring Harbor Laboratory Press, 2 ed., (1989); or F. Ausubel et al., CURRENT PROTOCOLS IN MOLECULAR BIOLOGY (Green Publishing and Wiley-Interscience: New York, 1987) and periodic updates).

Preferably, the IGF-binding protein or derivative is produced using a bacterial cell strain as the recombinant host cell. An expression construct (i.e., a DNA sequence comprising a sequence encoding the desired IGF-binding protein or derivative operably linked to the necessary DNA sequences for proper expression in the host cell, such as a promoter and/or enhancer elements at the 5' end of the construct and terminator elements in the 3' end of the construct) is introduced into the host cell. The DNA sequence encoding the IGF-binding protein or derivative may optionally linked to a sequence coding another protein (a "fusion partner"), to form a fusion protein. Preferably, the DNA sequence encoding the IGF-binding protein or derivative is linked to a sequence encoding a fusion partner as described in U.S. Pat. No. 5,914,254. The expression construct may be an extrachromosomal construct, such as a plasmid or cosmid, or it may be integrated into the chromosome of the host cell, for example as described in U.S. Pat. No. 5,861,273.

IGF-binding protein or derivative is preferably administered by parenteral administration, including but not limited to intravenous (IV), intraperitoneal (IP), intramuscular (IM), subcutaneous (SC), intradermal (ID), transdermal, inhaled, and intranasal routes. IV, IP, IM, and ID administration may be by bolus or infusion administration. For SC administration, administration may be by bolus, infusion, or by implantable device, such as an implantable minipump (e.g., osmotic or mechanical minipump) or slow release implant. The IGF-binding protein or derivative may also be delivered in a slow release formulation adapted for IV, IP, IM, ID or SC administration. Inhaled IGF-binding protein or derivative is preferably delivered in discrete doses (e.g., via a metered dose inhaler adapted for protein delivery). Administration of IGF-binding protein or derivative via the transdermal route may be continuous or pulsatile. Administration of derivatives may also occur orally.

For parenteral administration, compositions of IGF-binding protein or derivative may be in dry powder, semi-solid or liquid formulations. For parenteral administration by routes other than inhalation, the IGF-binding protein or derivative is preferably administered in a liquid formulation. IGF-binding protein or derivative formulations may contain additional components such as salts, buffers, bulking agents, osmolytes, antioxidants, detergents, surfactants, and other pharmaceutical excipients as are known in the art.

IGF-binding protein or derivative is administered to subjects having cancer at a dose of about 0.01 to about 40 mg/kg/day, more preferably about 0.1 to about 10 mg/kg/day, more preferably 0.5 to about 4 mg/kg/day, even more preferably about 1 to about 2 mg/kg/day.

As an alternative to administration of IGFBP or a derivative thereof, a nucleic acid construct encoding the IGFBP may be administered. The construct contains a polynucleotide sequence encoding the IGFBP, and normally contains sequences operably linked to the IGFBP sequence which result in expression and translation of the IGFBP sequence in the cells (e.g., a promoter/enhancer, translation initiation site, polyadenylation signal, etc.), although constructs which are designed to integrate into the cell chromosome are also contemplated (e.g., where the construct contains sequence which facilitates integration into the host chromosome, such as sequences homologous to the recipient cells' chromosome flanking the IGFBP sequence).

Methods of gene transfer are well known in the art, and include in vitro methods (e.g., transformation of cultured cells, preferably autologous cells, which are reintroduced into the subject), ex vivo methods (e.g., transformation of cells which have not been cultured in vivo, preferably autologous cells, with are reintroduced into the subject), and in vivo methods (e.g., transformation of cells in situ by administration of a nucleic acid construct to the subject). Methods for accomplishing such gene transfer are well known in the art, and include standard transformation methods including calcium phosphate transformation, ballistic transformation, electroporation, lipid-mediated transformation, naked DNA transfer, and viral-mediated transfer.

The IGF-binding protein or derivative is administered to the subject together with one or more of the following co-administered agents: a chemotherapeutic agent; an antibody; physical stress, such as radiation; or a ligand of a receptor present on the target cells, such as retinoid receptors and thyroid receptors. The administration of the two agents may be simultaneous, overlapping, or separated in time, as long as the subject experiences exposure to both agents at the same time. Where the two agents are formulated for the same route and schedule of administration, the administration is preferably simultaneous or nearly simultaneous (e.g., concurrent or serial injections). However, in some embodiments, the routes and schedules of administration for the two agents will be different, making simultaneous administration inconvenient. A subject will be considered to have been administered both agents if the subject experiences simultaneous systemic exposure to both compounds, regardless of when or how the compounds were administered.

In methods requiring the administration of co-administered agent with the IGF-binding protein or derivative, the dose of the co-administered agent is normally titrated for the individual subject, as is known in the art for that agent. Co-administered agents may be produced in any formulation known to the art, including parenteral and oral dosage forms. Oral formulations are preferred, but parenteral formulations are also acceptable, and may be more convenient in an in-patient setting. Formulations for parenteral administration are generally formulated as liquids, but may also be in gel or solid depot form. Formulations for oral administration are generally in tablet or capsule form, although syrups and liquids are also acceptable. Formulations of co-administered agents generally include excipients, such as salts, buffers, bulking agents, detergents, binding agents, surfactants, stabilizers, preservatives, anti-oxidants, lubricants, coating agents, and other pharmaceutically acceptable excipients as are known in the art.

The dosage and mode of administration of the co-administered agent should be adjusted according to the identity, formulation, route of administration and other relevant characteristics pertaining to the co-administered agent, as is known in the art.

Inducers and antagonists would be administered in a similar way. As an example: Where the antagonist is propylthiouracil, the dose of propylthiouracil may be from 1 to 400 mg/day. A subject is normally initiated with a dose of 50 to 400 mg/day, typically divided into three equal doses, and maintained at 50 to 100 mg/day divided into two or three equal doses. For methimazole and carbimazole, the dose may be from 0.1 to 50 mg/day. Typically, a subject is initiated with 5 to 50 mg/day, and maintained on 1 to 5 mg/day.

As will be understood by those of skill in the art, the symptoms of cancer alleviated by the instant methods, as well as the methods used to measure the symptom(s) will vary, depending on the particular cancer and the individual patient. For solid tumors, the most significant symptom is usually tumor size (either primary tumor size or metastasis size). Tumor size may be measured by any method known in the art, including radiological methods (e.g., x-ray, CT scan, MRI, PET scan, and the like), markers associated with tumor size (e.g., serum prostate specific antigen, or PSA, levels in prostate cancer, carcinoembryonic antigen, or CEA, levels in colon and other cancers, and the like), direct physical measurement, etc. Because many cancers, particularly advanced stage cancers, are physically debilitating, performance-based measurements such as activities of daily living (ADLs) or Karnofsky performance score are useful in measuring a patient's response to treatment. For tumors that secrete one or more hormones, serum levels of the hormone secreted by the tumor may be used as a marker of tumor size.

Many tumors induce physical symptoms due to their anatomic location, and these secondary symptoms are considered symptoms of the cancer. For example, bone tumors frequently cause significant bone pain, and colorectal tumors can result in blockage of the colon. These secondary symptoms can be measured using appropriate methods known in the art (e.g., visual scales for measurement of pain).

The invention also provides kits for use in the methods of the invention. Kits of the invention comprise one or more containers comprising IGFBP, and may optionally comprise one or more containers of a co-administered agent and/or a set of instructions, generally written instructions, relating to the use of IGFBP with a co-administered agent for the treatment of cancer.

The kits comprise IGFBP (and optional co-administered agent) in any convenient, appropriate packaging. For example, if the IGFBP or the co-administered agent is a dry formulation (e.g., freeze dried or a dry powder), a vial with a resilient stopper is normally used, so that the IGFBP or co-administered agent may be easily resuspended by injecting fluid through the resilient stopper. Ampoules with non-resilient, removable closures (e.g., sealed glass) or resilient stoppers are most conveniently used for liquid formulations of IGFBP or co-administered agent. Also contemplated are packages for use in combination with a specific device, such as an inhaler, nasal administration device (e.g., an atomizer) or an infusion device such as a minipump. While it is contemplated that the IGFBP and the co-administered agent can be supplied as a mixture, it is generally preferred that the IGFBP and the co-administered agent be supplied in separate containers.

The instructions relating to the use of IGFBP and co-administered agent for the treatment of cancer generally include information as to dosage, dosing schedule, and route of administration for the treatment. The containers of IGFBP (and optional co-administered agent) may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The patents, patent applications, and publications cited throughout the disclosure are incorporated herein by reference in their entirety.

EXAMPLES

Example 1

Treatment of Nutritionally Stressed A293 Kidney Cells with IGFBP-3

Human embryonal kidney A293 cells were grown in Dulbecco's Modified Eagle Medium (D-MEM) supplemented with fetal calf serum at 2%, 4%, 6%, or 8%. When the cells reached 80-85% confluency (cell titer approximately $2.1 \times 10^6$ cells per plate), 5 ug of IGFBP-3 or buffer control was added to each plate. The cells were incubated at 37 C overnight. The next day the medium was removed and the cells were rinsed with trypsin-EDTA (0.25% trypsin, 1 mM EDTA) plus 1× phosphate buffered saline. The cells were cetrifuged and the supernatant was removed. ApoAlert caspase-3 assay kit from Clontech Inc (Palo Alto, Calif.) was used to measure apoptosis. The cells were resuspended in 50 ul of chilled cell lysis buffer and incubated on ice for 10 minutes. The resulting cell lysates were centrifuged at 14000 rpm in a Beckman microcentrifuge for 3 minutes at 4 C. The supernatant was transferred to new tubes and 50 ul of 2× reaction buffer/DTT plus 5 ul of 1 mM caspase-3 substrate was added to each tube. After incubating at 37 C for 1 hour in a water bath, the samples were read at 405 nm in a microplate reader. The results of this experiment are shown in FIG. 2.

Example 2

Treatment of 16C Mammary Tumors with IGFBP-3 and Co-administered Agents

Female C3H mice (8-11 animals per group) received early SC implants of 16C mammary adenocarcinoma tumor fragments (near 100% "take") and were treated with vehicle, [N109D]-IGFBP-3 (4 mg/kg/day SC ×21), 5-FU (10 mg/kg/day IP ×5), adriamycin (2 mg/kg/dose IV on day 1 and day 8 post-implant), or the indicated combinations. Tumors were measured twice weekly. Animals were sacrificed at Day 21. The doses of doxorubicin and 5-fluorouracil used in this experiment were chosen to be marginally effective, based on previous experience with these chemical agents in this model. [N109D]-IGFBP-3 significantly (p<0.01) potentiated the effects of both agents, but had no measurable effects on its own. The results are shown graphically in FIG. 2. Table 1 below shows the delay (in days) in tumor growth (endpoint of 1500 mg tumor weight).

TABLE 1

| Treatment Group | Days Delay |
| --- | --- |
| CONTROL | 0 |
| [N109D]-IGFBP-3 ALONE | −0.2 |
| ADRIAMYCIN ® | +2.5* |
| ADRIAMYCIN ® + [N109D]-IGFBP-3 | +4.4** |
| 5-FLUOROURACIL | +1.9 |
| 5-FLUOROURACIL + [N109D]-IGFBP-3 | +3.1** |

*p < 0.05;
**p < 0.001

In order to gain further insights into the mechanism of action of exogenously added IGFBP-3 in these mouse models, tumor tissues from the groups treated with vehicle, doxorubicin, or doxorubicin plus IGFBP-3, were further analyzed using gene array technology. RNA was extracted from tumor tissue. cDNA was prepared, labelled and used to probe Atlas 1.2k-I mouse gene arrays (Clontech Laboratories Inc., Palo Alto, Calif.). These arrays contain 1,176 mouse gene sequences. The results indicated that adriamycin alone produced differential expression of 26 genes (2%), 16 of which were down-regulated. Interestingly, some of the latter included genes whose products are known agents in cell cycle checkpoint control, growth-related responses, as well as a number of cytoskeletal/extracellular matrix proteins. In general, adriamycin appears to blunt some of the very mechanisms that could hasten the demise of treated tumor cells, but these were normalized by IGFBP-3 co-treatment. Interestingly, RXR-alpha levels are 50% inhibited in tumors from animals treated with a combination of doxorubicin and IGFBP-3 (but not when treated with doxorubicin alone).

Example 3

Treatment of MDA-MB-231 Mammary Tumors with IGFBP-3 and Co-administered Agents

MDA-MB-231 tumors were implanted in nude mice. Ten animals (NCr-nu) were allocated to each group. The tumors were implanted SC as trocar fragments and allowed to increase in size to approximately 170 mg before treatment began on Day 15 post-implant. The treatment regimen for [N109D]-IGFBP-3 was 4.0 mg/kg/dose, daily for 21 days, SC beginning on Day 15. The treatment regimen for Taxol was 5.0 mg/kg/day, daily for five days, IV. The treatment regimen for Cisplatin was 4.0 mg/kg/dose, administered every fourth day for three treatments, IP. Treatment regimens for TAXOL® and Cisplatin began on Day 18. Tumor measurements were performed daily.

TABLE 2

| | MEDIAN TUMOR VOLUME IN MILLIGRAMS ON DAYS INDICATED | | | | | |
|---|---|---|---|---|---|---|
| | 15 | 19 | 22 | 26 | 29 | 33 |
| CONTROL | 171 ± 26 | 464 ± 244 | 694 ± 311 | 877 ± 664 | 1116 ± 858 | 1965 ± 1384 |
| IGFBP-3 | 161 ± 35 | 367.5 ± 244 | 565 ± 510 | 818.5 ± 750 | 1089 ± 851 | 1936 ± 1825 |
| CISPLATIN | 171 ± 33 | 368 ± 124 | 446 ± 175 | 563 ± 214 | 675 ± 220 | 922 ± 299 |
| CIS ± BP3 | 162 ± 37 | 384 ± 117 | 432 ± 173 | 608 ± 316 | 649 ± 347 | 908 ± 516 |
| TAXOL ® | 153 ± 32 | 327 ± 131 | 384 ± 337 | 512 ± 489 | 648 ± 538 | 900 ± 1067 |
| TAXOL ® + BP3 | 162 ± 44 | 302 ± 192 | 416 ± 241 | 416 ± 262 | 432 ± 351 | 513 ± 757 |

Cisplatin and TAXOL® groups and combination groups were significantly different from control. [N109D]-IGFBP-3 group was not significantly different from control. Strong synergistic effects were seen in the TAXOL®+IGFBP-3 combination treatment compared to TAXOL® alone, but not in the cisplatin+IGFBP-3 combination compared to cisplatin alone. The results are shown in FIG. 3. Table 3 below shows the delay (in days) in tumor growth (endpoint of 3× doubling of tumor weight).

TABLE 3

| Treatment Group | Days Delay |
|---|---|
| CONTROL | 0 |
| [N109D]-IGFBP-3 ALONE | −2.2 |
| TAXOL | +3.5 |
| TAXOL + [N109D]-IGFBP-3 | >+8.9* |

*$p < 0.05$;

Example 4

Treatment of LAPC-4 Prostate Tumor Cells with IGFBP-3 and Co-administered Agents A study was performed to analyze the effects of IGFBP-3 in combination with Taxol on the growth and death of prostate cancer cells utilizing the LAPC-4 xenograft model. One million cells (in 100 mcl) were injected SQ into SCID mice. After 4 weeks palpable tumors were observed. 4 groups were treated (6 mice per group): 1) saline control; 2) IGFBP-3 (4 mg/kg/day intra-peritoneally); 3) taxol (2 mg/kg/day intra-peritoneally on days 5 through 8); 4) taxol and IGFBP-3 combination. Tumors were analyzed for size by palpation weekly and serum collected. Animals were sacrificed at day 21 and tumor weight assessed. The results of this experiment demonstrated a trend for reduced tumor size (40%) with combination therapy.

Example 5

Generation of Defined Sub-domains of IGFBP-3 by Engineering 3C Protease Target Sites into the Primary Sequence of the Protein Defined IGFBP-3 sub-domains were generated from constructs expressed as soluble fusion proteins in an *E. coli* expression system. The general structures of the fusions are:

IVS-1: DsbA(mut) . . . [3C] . . . domain 1 . . . [3C] . . . domain 2/3

IVS-2: DsbA(mut) . . . [3C] . . . domain 1/2 . . . [3C] . . . domain 3 where [3C] is the peptide sequence recognized by HRV 3C proteinase. Yields are comparable to wild type, and a substantial fraction is believed to be correctly folded, based on the demonstrated ability of the protein to bind IGF-I. After cleavage, the sub-domains of IGFBP-3 generated from the IVS-1 construct (domains 1, 2/3) are captured on hydrophobic interaction resins such as Phenyl-Sepharose or (less desirably) on cation exchange resins such as SP-Sepharose. Other resins, such as immobilized heparin can also be used. Efficient on-column cleavage of IVS-1 fusion with 3C proteinase has been demonstrated using 1:10 (protease to substrate) ratios at 4 degrees Celsius or room temperature. Complete cleavage has been seen in less than 20 minutes. In the past, amino acid sequencing of cleavage products has shown that the enzyme cleaves in an unusually clean manner (<5% "ragged" ends). From 2 grams of wet cell paste, a few milligrams of purified IGFBP-3 2/3 domain can be captured on Phenyl-Sepharose. Further purification to near homogeneity can be achieved on nickel- or zinc-affinity chromatography, as this invention further demonstrates, for the first time, the metal binding properties of IGFBP-3 and, furthermore, that the determinants of this characteristic of the protein are located primarily in the C-terminal portion of the molecule (i.e. the 2/3 domain). Apparently, metal-binding does not require the amino-terminal ~100 amino acids of the protein. The amino-terminal ~100 amino acids are deemed to constitute the primary domain for IGF-I binding in the IGFBP-3 molecule.

The present invention has been detailed both by direct description and by example. Equivalents and modifications of the present invention will be apparent to those skilled in the art, and are encompassed within the scope of the invention.

The invention claimed is:

1. An insulin-like growth factor binding protein-derived peptide said peptide consist of a sequence selected from the group consisting of DKKGFYKKKQCRPSKGRKRGFCW
(SEQ ID NO: 1)
and

QCRPSKGRKRGFCW
(SEQ ID NO: 2).

2. The peptide of claim 1, wherein said peptide consists of the sequence QCRPSKGRKRGFCW (SEQ ID NO: 2).

* * * * *